United States Patent [19]

Allen

[11] 4,394,522
[45] Jul. 19, 1983

[54] CATALYTIC HYDROGENATION OF DI(4-AMINOPHENYL)METHANE

[75] Inventor: Gary F. Allen, New Martinsville, W. Va.

[73] Assignee: Mobay Chemical Corporation, Pittsburgh, Pa.

[21] Appl. No.: 268,979

[22] Filed: Jun. 1, 1981

[51] Int. Cl.³ ............................................. C07C 85/24
[52] U.S. Cl. ..................................... 564/451; 564/450
[58] Field of Search ............................... 564/451, 450

[56] References Cited

U.S. PATENT DOCUMENTS

| | | | |
|---|---|---|---|
| 2,494,563 | 1/1950 | Kirk, Jr. et al. | 260/563 |
| 2,606,924 | 8/1952 | Whitman | 260/563 |
| 2,606,925 | 8/1952 | Whitman | 260/563 |
| 2,606,928 | 8/1952 | Barkdoll et al. | 260/563 |
| 3,153,088 | 10/1964 | Arthur | 260/563 |
| 3,155,724 | 11/1964 | Arthur | 260/563 |
| 3,330,850 | 7/1967 | Campbell et al. | 260/453 |
| 3,347,917 | 10/1967 | Arthur | 260/563 |
| 3,361,814 | 1/1968 | Campbell et al. | 260/563 |
| 3,393,236 | 7/1968 | Kuszewski | 260/563 |
| 3,557,180 | 1/1971 | Hoeschele | 260/453 |
| 3,590,002 | 6/1971 | Powers | 252/182 |
| 3,636,108 | 1/1972 | Brake | 260/563 D |
| 3,644,522 | 2/1972 | Brake et al. | 260/563 D |
| 3,676,495 | 7/1972 | Hoeschele | 260/563 R |
| 3,711,550 | 1/1973 | Brake | 260/563 B |
| 3,742,049 | 6/1973 | Komoto et al. | 260/563 D |
| 3,743,677 | 7/1973 | Grosskinsky et al. | 260/563 D |
| 3,766,272 | 10/1973 | Brake | 260/563 B |
| 3,825,586 | 7/1974 | Traumann | 260/501.2 |
| 3,914,307 | 10/1975 | Massie | 260/563 B |
| 3,959,374 | 5/1976 | Brennan et al. | 260/563 B |
| 4,161,492 | 7/1979 | Weissel | 260/563 R |
| 4,226,737 | 10/1980 | Kluger et al. | 252/182 |

Primary Examiner—John Doll
Attorney, Agent, or Firm—Gene Harsh; Joseph C. Gil; Richard A. Elder

[57] ABSTRACT

The present invention relates to an improved process for the catalytic hydrogenation of di(4-aminophenyl)methane to a liquid di(4-aminocyclohexyl)methane mixture containing from 15 to 40% by weight and preferably from 18.5 to 23.5% by weight, of the trans, trans isomer. The invention resides in the use of an unsupported ruthenium dioxide catalyst under specific process conditions. During the hydrogenation reaction, a pressure of at least 2500 psi and a temperature of from 150° to 210° C. must be maintained.

10 Claims, No Drawings

CATALYTIC HYDROGENATION OF DI(4-AMINOPHENYL)METHANE

BACKGROUND OF THE INVENTION

In the production of di(4-aminocyclohexyl)methane by the catalytic hydrogenation of di(4-aminophenyl)methane, essentially three stereoisomers are produced.

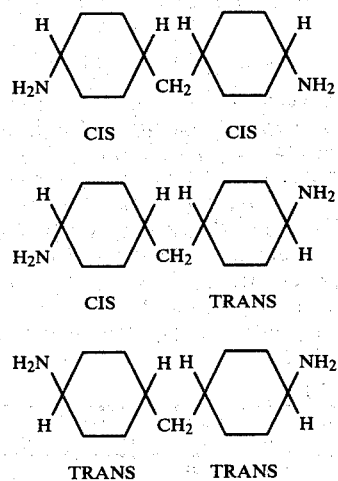

It is known in the art that in order to produce a corresponding isocyanate (via the known phosgenation process) which is liquid and storage stable at room temperature (i.e. from 20° to 25° C.), the mixture of amine stereoisomers used for phosgenation must contain the trans, trans stereoisomer in relatively narrow amounts (typically from 15 to 40 percent by weight, and preferably from 18.5 to 23.5 percent by weight).

Numerous techniques are known in the art for the production of amine mixtures containing the requisite amount of the trans, trans isomer. Typical of these known techniques are those described in U.S. Pat. Nos. 3,153,088; 3,155,724; 3,393,236; 3,644,522; 3,711,550 and 3,766,272. These known techniques generally require the separation of an amine mixture containing the requisite amount of the trans, trans isomer from an amine mixture formed after hydrogenation and containing around 50% by weight of the trans, trans isomer. Processes are known in the art for the production of a di(4-aminocyclohexyl)methane mixture containing the requisite amount of the trans, trans isomer directly from di(4-aminophenyl)methane without the need for an intermediate separation step (see e.g. U.S. Pat. No. 2,606,928). However, the rates of reaction are much too slow for commercial application.

Numerous processes are known in the art for the production of di(4-aminocyclohexyl)methane from di(4-aminophenyl)methane via catalytic hydrogenation using supported and unsupported ruthenium catalysts. Typical of these processes are those disclosed in U.S. Pat. Nos. 2,494,563; 2,606,924; 2,606,928; 2,606,925; 3,347,917; 3,676,495; 3,959,374; 3,743,677; 3,914,307; 3,825,586; 3,636,108 and 4,161,492. While some of these processes yield an amine mixture containing the trans, trans isomer in an amount necessary to allow for the production of an isocyanate which is liquid and storage stable at room temperature, the rates of reaction are much too slow for commercial use.

Ruthenium based catalysts have also been described as being useful in the hydrogenation of (a) polycycloaromatic polyamines formed from aniline and formaldehyde (see U.S. Pat. No. 4,226,737); (b) 2,4-bis(p-amino benzyl)aniline (see U.S. Pat. No. 3,557,180); (c) 2,4'-diaminodiphenylmethane (see (U.S. Pat. No. 3,590,002); and (d) tolylene diamine/formaldehyde condensates (see U.S. Pat. Nos. 3,330,850 and 3,361,814). However, none of these processes relate to the present problems, i.e., production of a di(4-aminocyclohexyl)methane containing the trans, trans stereoisomer in the amount required.

Finally, the use of a specific amorphous form of ruthenium oxide has been described for the production of di(4-aminocyclohexyl)methane from di(4-nitrophenyl)methane. (See e.g., U.S. Pat. No. 3,742,049).

DESCRIPTION OF THE INVENTION

The present invention is directed to the discovery that liquid di(4-aminocyclohexyl)methanes containing from 15 to 40 percent by weight and preferably from 18.5 to 23.5% by weight of the trans, trans isomer can be produced directly from di(4-aminophenyl)methane by using an unsupported ruthenium dioxide catalyst and by using specific process conditions. Specifically, the hydrogen pressure must be maintained at at least 2500 psi and the temperature must be maintained at from 150° C. to 210° C. during the hydrogenation.

The catalysts employed are generally known and are commercially available. The presently preferred catalysts are two hydrated ruthenium dioxide catalysts available from Engelhard (one containing 40.9% ruthenium and the other containing 58.3% ruthenium), and a Johnson-Matthey hydrated ruthenium dioxide.

In conducting the process of the invention, the procedures commonly used in the art are employed, the only requirements being the pressure and temperature conditions noted above. The hydrogenation is preferably carried out in the presence of an inert solvent, i.e., a solvent which does not substantially interfere with the desired course of the hydrogenation.

Useful solvents include ethers such as isopropyl ether or n-butyl ether; cyclohexane and other aliphatic hydrocarbons; alcohols such as butyl alcohol, methanol, ethanol, isopropanol, propanol and the like; and cyclic ethers such as tetrahydrofuran, dioxane, and the like. The amount of solvent used can range from 0 to 95% by weight based on the amount of amines and solvent. Preferably the amount of solvent used is such that the concentration of starting diamine in the reaction mixture is from about 5% to about 50% by weight. The presently preferred solvent is n-butyl ether.

The catalyst is suspended in a solution of the starting diamine and the resulting suspension is subjected to hydrogenation in an appropriate hydrogenation vessel. The amount of catalyst employed is such that the amount of ruthenium metal present in the reaction mixture is at least 0.05% by weight and preferably within the range of about 0.1 to about 3% by weight based on the amount of starting diamine present in the reaction mixtures. As noted above, the amount of catalyst should be at least 0.05%. Economics generally dictate the upper limit since the catalyst is generally expensive. Preferably the quantity of catalyst employed is such that the amount of ruthenium present in the reaction mixture is within the range of from about 0.1 to about 1% by weight based on the amount of starting diamine employed.

The hydrogenation is conducted at a temperature within the range of 150° to 210° C. The exact choice of temperature in any given instance is a function of the reaction rate and the trans, trans content desired. In general, the higher the temperature, the faster the reaction rate and the higher the trans, trans content of the final product. Thus, the temperature will generally be selected to yield the best balance of reaction time and trans, trans content.

The hydrogenation pressure employed in the process of the invention must be maintained at at least 2500 psi and will generally be between 2500 and 4000 psi. Of course, the pressures used are generally dependent on the equipment used. Thus, pressures of from 2500 to 8000 psi and higher can be used if suitable high pressure equipment is available. In general, it has been found that the yield will increase with increasing pressure.

The progress of the hydrogenation is followed readily by observation of the amount of hydrogen taken up by the reaction mixture and the hydrogenation is terminated at the point at which the theoretical quantity of hydrogen has been absorbed. The catalyst is then separated from the solution of reduced material and the latter is distilled to isolate the di(4-aminocyclohexyl)methane therefrom. In general, the hydrogenation times range from about 30 minutes to about 90 minutes.

Although not necessary to obtaining results of the present invention, if desired, ammonia can also be used as described in several of the patents noted above (see, e.g., U.S. Pat. Nos. 3,347,917; 3,636,108 and 3,644,522).

In general, the materials are mixed and added to the reactor in a batch process, but, of course, a continuous process could also be used.

The invention is further illustrated, but is not intended to be limited by the following Examples in which all parts and percentages are by weight unless otherwise specified.

EXAMPLES

Examples 1 Through 8

200 parts of n-butyl ether, 200 parts of di(4-aminophenyl)methane and the amount of Engelhard hydrated ruthenium dioxide (containing 58.3% ruthenium) noted in Table 1 were added to a high pressure autoclave. The autoclave was sealed and pressurized to 4000 psi of hydrogen, and the contents were heated to the temperature noted in Table 1. The reaction was maintained at the specified temperature for thirty minutes after hydrogen consumption stopped. The contents of the autoclave were removed at room temperature and vacuum filtered. The products were analyzed for trans, trans content and were characterized as being liquid or not, with the results as set forth in Table 1.

TABLE 1

| Example | Catalyst Amt., pbw | % by wt. of Ru Metal | Temp. °C. | % t/t | Liquid | Yield % by HPLC |
|---|---|---|---|---|---|---|
| 1 | 3 | 0.81 | 150 | 18.5 | Yes | 44 |
| 2 | 1 | 0.27 | 180 | 20.5 | Yes | 95 |
| 3 | 1 | 0.27 | 196 | 22.3 | Yes | 95 |
| 4 | 1 | 0.27 | 200 | 21.3 | Yes | 64 |
| 5 | 1 | 0.27 | 202 | 26.4 | Yes | 73 |
| 6 | 1 | 0.27 | 204 | 27.7 | Yes | 74 |
| 7 | 1 | 0.27 | 208 | 30.7 | Yes | 70 |
| 8 | 1 | 0.27 | 215 | 49.1 | No | 86 |

Examples 9 Through 13

In a manner similar to Examples 1 through 8, n-butyl ether, di(4-aminophenyl)methane and Engelhard hydrated ruthenium dioxide (containing 58.3% ruthenium) were added to a high pressure autoclave. The catalyst used was mixed with the ether and held for one hour at 200° C. and 2000 psi prior to introduction of the amine. The conditions of reaction and amounts of material were as set forth in Table 2, with the pressures noted being maintained at that level throughout the reaction. The yields and trans, trans content were as set forth in Table 2.

TABLE 2

| Example | Temp °C. | Pres. psi | Catalyst pbw | % by wt. of Ru metal | Ether pbw | Amine pbw | H₂ Times min. | Yield, % by HPLC | % t/t |
|---|---|---|---|---|---|---|---|---|---|
| 9 | 210 | 4000 | 0.37 | 0.11 | 200 | 200 | 70 | 90.3 | 36.3 |
| 10 | 210 | 4000 | 0.37 | 0.11 | 200 | 200 | 60 | 87.5 | 31.1 |
| 11 | 210 | 4000 | 0.56 | 0.11 | 150 | 300 | 30 | 86.6 | 26.3 |
| 12 | 210 | 4000 | 1.39 | 0.27 | 150 | 300 | 31 | 90.4 | 37.3 |
| 13 | 210 | 2000 | 0.56 | 0.11 | 150 | 300 | 90 | 40.0 | 30.7 |

What is claimed is:

1. A process for the catalytic hydrogenation of di(4-aminophenyl)methane to a liquid di(4-aminocyclohexyl)methane containing from 15% to 40% by weight of the trans, trans isomer comprising hydrogenating di(4-aminophenyl)methane in the presence of an unsupported ruthenium dioxide catalyst under a hydrogen pressure of at least 2500 psi and at a temperature of from 150° to 210° C.

2. The process of claim 1 wherein the trans, trans isomer content is from 18.5 to 23.5% by weight.

3. The process of claim 1 wherein the hydrogenation is conducted in the presence of from 0 to 95% by weight of a solvent which is inert under the reaction conditions.

4. The process of claim 3 wherein said solvent is n-butyl ether.

5. The process of claim 3 wherein said solvent is used in an amount such that the concentration of the starting diamine is from about 5 to about 50% by weight.

6. The process of claim 1 wherein the catalyst is present in an amount such that the amount of ruthenium metal present is at least 0.05% by weight based on the amount of starting diamine.

7. The process of claim 6 wherein the amount of catalyst present is such that the amount of ruthenium metal is from about 0.1 to about 3% by weight.

8. The process of claim 1 wherein the hydrogen pressure is from 2500 to 4000 psi.

9. The process of claim 1 wherein the hydrogen pressure is from 2500 to 8000 psi.

10. The process of claim 1 wherein the reaction is conducted for a period of from about 30 minutes to about 90 minutes.

* * * * *